(12) United States Patent
Larsen et al.

(10) Patent No.: US 11,633,453 B2
(45) Date of Patent: Apr. 25, 2023

(54) RECONSTITUTABLE TEVERELIX-TFA COMPOSITION

(71) Applicant: Antev Limited, London (GB)

(72) Inventors: Finn Larsen, Hawick (GB); Francois Boutignon, Clermont-Ferrand (FR); Guy Poland, Bristol (GB)

(73) Assignee: Antev Limited, London (GB)

( * ) Notice: Subject to any disclaimer, the term of this patent is extended or adjusted under 35 U.S.C. 154(b) by 0 days.

(21) Appl. No.: 17/254,859

(22) PCT Filed: Jul. 2, 2019

(86) PCT No.: PCT/EP2019/067718
§ 371 (c)(1),
(2) Date: Dec. 22, 2020

(87) PCT Pub. No.: WO2020/007852
PCT Pub. Date: Jan. 9, 2020

(65) Prior Publication Data
US 2021/0236587 A1 Aug. 5, 2021

(30) Foreign Application Priority Data
Jul. 5, 2018 (EP) .................................... 18181931

(51) Int. Cl.
| | | |
|---|---|---|
| *A61K 9/19* | (2006.01) | |
| *A61K 38/09* | (2006.01) | |
| *A61K 9/00* | (2006.01) | |
| *A61K 47/12* | (2006.01) | |

(52) U.S. Cl.
CPC ............ *A61K 38/09* (2013.01); *A61K 9/0019* (2013.01); *A61K 9/19* (2013.01); *A61K 47/12* (2013.01)

(58) Field of Classification Search
CPC .................................. A61K 38/09; A61K 9/19
See application file for complete search history.

(56) References Cited

U.S. PATENT DOCUMENTS

2003/0044463 A1    3/2003  Deghenghi et al.

FOREIGN PATENT DOCUMENTS

| WO | WO2003/022243 A2 | 3/2003 |
| WO | WO2008/071984 A1 | 6/2008 |

OTHER PUBLICATIONS

Derek Duncan, BioPharma International, (2016).*
International Search Report and Written Opinion Appl. No. PCT/EP2019/067718, dated Jul. 2, 2019.
International Preliminary Report on Patentability (IPRP), Appl. No. PCT/EP2019/067718, dated Jun. 19, 2020.

* cited by examiner

*Primary Examiner* — Gyan Chandra
(74) *Attorney, Agent, or Firm* — Fox Rothschild LLP

(57) ABSTRACT

The present invention relates to a reconstitutable teverelix-TFA composition having a predefined molar ratio of teverelix to trifluoroacetate which is below the molar ratio required for microcrystal formation. Said composition remains stable during storage e.g. at a temperature around 2-8° C. Upon reconstitution a fixed amount of trifluoroacetate can be added to said composition thereby effectively and simply achieving an exact and desired molar ratio in order to obtain a fluid, milky microcrystalline aqueous teverelix-TFA suspension.

12 Claims, 6 Drawing Sheets

Microscopy of suspension A1

Microscopy of suspension B1

Microscopy of suspension C1

Microscopy of suspension D1

Microscopy of suspension E1

Microscopy of suspension F1

Microscopy of suspension G1

RECONSTITUTABLE TEVERELIX-TFA COMPOSITION

This application is a 371 filing of International Patent Application PCT/EP2019/067718 filed Jul. 2, 2019, which claims the benefit of European patent application no. 18181931.9 filed Jul. 5, 2018.

TECHNICAL FIELD

The present invention relates to a reconstitutable teverelix-TFA composition, a method of preparing said composition and a method of reconstituting said composition.

BACKGROUND

Teverelix is a synthetic gonadotropin-releasing hormone antagonists (GnRH antagonists) that compete with the endogenous neurohormone GnRH (otherwise known as luteinizing hormone releasing hormone, LHRH) for binding to its receptors in the anterior pituitary gland. By decreasing or blocking GnRH action, the GnRH antagonist suppress release from the anterior pituitary gland of follicle stimulating hormone (FSH) and luteinizing hormone (LH).

Both FSH and LH are involved in normal reproductive function. In females, FSH stimulates the growth of immature Graafian follicles to maturation, whereas changes in LH levels control ovulation. In males, on the other hand, FSH plays an important role in spermatogenesis and LH stimulates production of testosterone in the testes.

Accordingly, teverelix is suitable for treatment of hormone-dependent conditions such as benign prostatic hypertrophy, hormone-dependent prostate cancer, endometriosis and uterine myomas.

Since teverelix (Ac-D-Nal-D-pClPhe-D-Pal-Ser-Tyr-D-Hci-Leu-Lys(iPr)-Pro-D-Ala-$NH_2$) is a hydrophobic peptide it has a tendency of forming gels in the presence of many counter-ions. This problem has been solved in WO 2003/022243 which discloses that the formation of a gel may be prevented by contacting the teverelix peptide with a counter-ion, e.g. trifluoroacetate (TFA), at a molar ratio of at least 1:1.6 of peptide to counter-ion, thereby providing a fluid, milky microcrystalline aqueous suspension of the teverelix-salt (e.g. teverelix-TFA).

According to WO 2003/022243, a ratio of teverelix to the counter-ion trifluoroacetate (TFA) of at least 1:1.6 is essential in order to ensure the desired microcrystalline suspension is obtained, otherwise a gel will be formed. However, the inventors of the present invention have found that the molar ratios disclosed in WO 2003/022243 will result in both undesirable gel-formation and in suspensions which are not homogenous. This is a problem, not only because such suspensions will be difficult to inject, but also because the bioavailability of the teverelix peptide is compromised since the gel interferes with the desired sustained action of said peptide.

Since teverelix is deamidated when placed in contact with water and acid, the teverelix-TFA compositions of WO 2003/022243 is not stable during storage e.g. at refrigeration and room temperatures and accordingly the teverelix composition has a relatively short shelf life under such conditions.

Deamidation is caused by hydrolysis of the teverelix peptide. However, since a reduction in the water content may contribute to an increased rate of deamidation, e.g. due to a lower pH-value in the composition, it would not be obvious to reduce the water content in the composition in order to increase the shelf life.

Another problem with the teverelix-TFA compositions disclosed in WO 2003/022243 is that the inventors of the present invention has discovered that there are batch variations in the molar ratio of teverelix to the counter-ion TFA provided by the manufactures, even though the applied manufacturing conditions and processes are identical.

Since the molar ratio is essential for obtaining the desired microcrystalline suspension, variations in said ratio may affect the bioavailablity of teverelix in the pharmaceutical formulations. It is therefore essential that medical personal and other users can rely on the molar ratio of teverelix to trifluoroacetate provided by the manufactures.

Accordingly, there is a demand to both develop stable compositions having a long shelf life, and provide new methods of manufacturing teverelix-TFA in which a predefined molar ratio of peptide to counter-ion is obtained and which corresponds to the expectations.

SUMMARY OF THE INVENTION

Thus, it is a first aspect of the present invention to provide teverelix-TFA composition having a prolonged shelf-life at refrigerating and room temperature.

It is a second aspect of the present invention to provide a method of ensuring that the desired molar ratio of peptide to counter-ion is obtained.

It is a third aspect of the present invention to provide a method of adjusting the molar ratio of peptide to counter-ion in a solution.

It is a fourth aspect of the present invention to provide teverelix-TFA compositions that exhibit a long duration of action, with a lower injection volume and which further allow for less frequent administration.

These and further aspects are achieved according to the present invention by providing a reconstitutable teverelix-TFA composition having a molar ratio of teverelix to trifluoroacetate which is below the molar ratio required for microcrystal formation.

Since the reconstitutable composition according to the invention has a low content of the counter-ion trifluoroacetate the pH value in the reconstitutable composition is maintained at a value which ensures that the deamidation of teverelix is reduced to an acceptable level, i.e. the possible deamidation which will take place is reduced to a level where it will not affect the stability of teverelix, whereby teverelix remains stable during storage e.g. at a temperature around 2-8° C.

It is in this respect preferred that the molar ratio of teverelix to trifluoroacetate in the reconstitutable composition is between 1:1 and 1:1.85, preferably around or below 1:1.6, as this will provide a stable reconstitutable teverelix-TFA composition.

Within the content of the present invention the term "molar ratio of teverelix to trifluoroacetate" refers to the molar relationship between teverelix and trifluoroacetate, where the first number of the molar ratio is the mol content of teverelix in the composition and the second number refers to the mol content of TFA in the composition. For instance, a molar ratio of 1:1.85 means that for each mol teverelix in the composition, said composition comprises 1.85 mol TFA. In a similar way will a molar ratio of at least 1:2.2 mean that for each mole teverelix in the composition, the composition comprises at least 2.2. mol trifluoroacetate (TFA).

In a preferred embodiment the molar ratio of teverelix to trifluoroacetate (TFA) is above 1:1.3 and below 1:1.6, i.e.

when the composition comprises 1 mol of teverelix, the content of TFA is between 1.3 and 1.6 mol, as the inventors of the present invention has found that molar ratios in this range provides an optimal stability of the reconstitutable teverelix-TFA composition.

The term "reconstitutable teverelix-TFA composition" refers to a substantially dry teverelix-TFA composition, preferably a powder, a lyophilizate, a cake, or a combination of these, and wherein said composition, after addition of a reconstitution liquid, is dissolved and/or suspended in said liquid.

Reconstitutable compositions are well known in the pharmaceutical industry, where water or another diluent is added to the dry composition immediately prior to administration. Such conventional reconstitutable compositions are stored in a substantially dry state in order to maintain the stability of the composition. The inventors of the present invention have however found that if a small amount of water is present in the reconstitutable compositions, i.e. in an amount between 0.3% to 5% by weight, preferably around 1 to 2% by weight, based on the total weight of the reconstitutable teverelix-TFA composition, an improved teverelix-TFA composition is provided which is easier to handle, reconstitute, and accordingly use.

Without being bound by theory, the water content may provide high electrostatic forces between particles of teverelix, which is of importance when the reconstitutable composition is handled e.g. when the composition is filled to a vial or a syringe chamber.

In a preferred embodiment water is present in the reconstitutable teverelix-TFA composition in an amount between 1% by weight and 2% by weight, preferably 1.5% by weight, based on the total weight of the reconstitutable teverelix-TFA composition, as this will provide a reconstitutable teverelix-TFA composition that retains its chemical integrity and provides a stable composition.

The stability provided by the invention enables a longer shelf-life at room temperature so that the reconstitutable teverelix-TFA composition may be stored e.g. after sterilization. The reconstitutable composition can be packaged and stored (e.g., in a syringe or vial) for later use.

The reconstitutable composition according to the invention may be prepared/manufactured in any suitable way, but in one embodiment teverelix and trifluoroacetate are contacted in an aqueous solution in order to provide an aqueous teverelix-TFA solution, which then is dried, e.g. to a powder, e.g. by freeze-drying (lyophilization) or spray drying, in order to provide the reconstitutable composition according to the invention. Thus, in a preferred embodiment the reconstitutable composition is a powder obtained by lyophilization (freeze-drying) or spray drying, and/or a cake obtained by lyophilization. The teverelix and trifluoroacetate are in one embodiment contacted at a predefined molar ratio which is below the molar ratio required for microcrystal formation, preferably above 1:1.3 and below 1:1.6.

In a preferred embodiment the drying step is ceased when the reconstitutable composition, e.g. powder contains water in an amount between 0.3% to 5% by weight based on the total weight of the reconstitutable teverelix-TFA composition. Preferably the solution is dried such that water is present in the reconstitutable teverelix-TFA composition in an amount between 1% by weight and 2% by weight, e.g. 1.5% by weight. The amount of water in said composition may e.g. be evaluated at the end of the drying period using conventional measuring methods and equipment.

As discussed earlier batch variations in the molar ratio of teverelix to trifluoroacetate may, for unknown reasons, arise during manufacturing, however it is preferred to know the exact molar ratio of teverelix to trifluoroacetate in a specific reconstitutable teverelix-TFA composition. Accordingly, the method of manufacturing the reconstitutable teverelix-TFA composition may further comprise the step of analysing the molar ratio in the solution prior to drying, such that the specific molar ratio is known. This will also provide the possibility of adjusting said molar ratio to a specific predefined molar ratio by adding trifluoroacetate before the solution is dried, thereby effectively counteracting any variation in the molar ratio that may exist. Thus, if the molar ratio is found to be e.g. 1:1.2 in the solution, said molar ratio may be adjusted to 1:1.4 by adding trifluoroacetate. The only requirement being that the resultant molar ratio before drying has to be below the molar ratio required for microcrystal formation.

The molar ratio of the solution may be determined by first measuring the content of trifluoroacetate and teverelix in the sample using a conventional HPLC method, and then calculating the molar ratio using the following formula:

$$\text{Molar ratio} = \frac{\text{trifluoroacetate content in solution}/M_{TFA}}{\text{teverelix content in solution}/M_{Tev}}$$

The molar mass of trifluoroacetate and teverelix has been calculated to: $M_{TFA}=114$ g/mol and $M=_{Tev}=1459$ g/mol.

After drying the thereby obtained reconstitutable teverelix-TFA composition may be stored and reconstituted with water or another suitable solution when an injectable pharmaceutical formulation is to be prepared.

Providing a reconstitutable teverelix-TFA composition according to the invention with a specific and predefined molar ratio will ensure that a fixed amount of trifluoroacetate can be added to said composition upon reconstitution thereby effectively and simply achieving an exact and desired molar ratio in order to obtain the fluid, milky microcrystalline aqueous suspension of the teverelix salt: teverelix-TFA, without formation of a gel. It is in this respect preferred that the molar ratio of teverelix to TFA after reconstitution is adjusted to at least 1:2.1 as the inventors have shown that a teverelix-TFA microcrystal suspension without formation of a gel thereby is obtained. When the ratio is above 1:2.2 the suspension is also homogeneous.

Thus, the low molar ratio of teverelix to the counter-ion trifluoroacetate in the reconstitutable composition according to the invention will, in addition to optimising the stability of the teverelix peptide, also ensure that it is possible to adjust the molar ratio of peptide to trifluoroacetate during the reconstitution process thereby ensuring that the optimal molar ratio of peptide to counter-ion may be obtained (depending on the intended use of the reconstituted composition) simply by adding the sufficient amount of trifluoroacetate during or after reconstitution.

For instance, if during the manufacturing process it has been established that the reconstitutable teverelix-TFA composition has a molar ratio of 1:1.4, and if a molar ratio of 1:2.2 is desired in the final aqueous teverelix-TFA formulation, then 0.8 mol TFA per mol teverelix present in the composition has to be added during the reconstitution process. Said amount can easily be calculated by a person skilled in the art.

A person skilled in the art will further understand that as long as the molar ratio of teverelix to trifluoroacetate is below the molar ratio required for microcrystal formation, it is of no relevance if said molar ratio is e.g. 1:1.4 or 1:1.36 as long as said ratio is known or can be calculated, in order to ensure that a person skilled in the art can calculate the correct amount of TFA to be used during the reconstitution process.

The trifluoroacetate content may be added/adjusted after the composition is reconstituted, but in a preferred embodiment the trifluoroacetate is part of the aqueous reconstitution solution, as this will provide a fast and effective way of reconstituting the composition according to the invention. If desired, the aqueous reconstitution solution may contain an isotonic agent, such as mannitol and/or a pharmaceutically acceptable excipient.

A person skilled in the art will based on the present application understand that instead of drying the teverelix-TFA solution in order to obtain a reconstitutable teverelix-TFA composition, the molar ratio can be adjusted directly in the solution to a molar ratio of teverelix to trifluoroacetate which is above the molar ratio required for microcrystal formation, i.e. above a ratio of 1:2.1, preferably at least 1:2.2 and even more preferred at least 1:2.4 after having evaluated the exact molar ratio, by adding a sufficient amount of trifluoroacetate. This will provide an aqueous pharmaceutical formulation that may be used directly, i.e. the formulation is ready-to-use.

The inventors of the present invention have furthermore found that when the molar ratio of teverelix to trifluoroacetate is at least 1:2.1, preferably at least 1:2.2, in the final aqueous pharmaceutical formulation, the formulation will comprise both soluble and insoluble teverelix, thereby providing a unique bioavailablity of teverelix.

Without being bound by theory, the soluble teverelix is in the form of an aqueous solution and in some situations, a gel. The presence of a gel will inhibit any freely aqueous teverelix and therefore prevent, or at least reduce, immediate release. The insoluble teverelix is in the form of microcrystals. Said microcrystals will prevent gel formation, therefore "unlocking" the aqueous teverelix. Over time the TFA in the composition according to the invention will be absorbed by the body, lowering the ratio, so the microcrystals subsequently turn in to gel, which forms the slow release depot. Thus, the non-gel-soluble teverelix is immediately available, providing an almost immediate onset of action, and the gel-soluble and insoluble teverelix (microcrystals) will assist in providing a sustained release of teverelix.

Accordingly, using the teverelix-TFA composition according to the invention, it is possible to adjust the release profile of teverelix simply by adjusting the amount of trifluoroacetate added to the reconstitutable composition and thereby change the ratio of insoluble to soluble teverelix in the injected composition.

Even though it is preferred that the teverelix TFA composition is stored in a dry state, e.g. as a powder obtained by lyophilization or spray-drying, it may be necessary to allow the final aqueous pharmaceutical formulation to be stored for a certain period of time. However, since teverelix is deamidated when placed in contact with water and high concentrations of acid, undesirable degradation products (impurities) will appear within the formulation in small amounts and may potentially influence quality, safety and efficacy of said formulation, thereby potentially causing serious health hazards.

The inventors of the present invention have found that the level of impurities are kept at an acceptable level, when the molar ratio of teverelix to TFA is below 1:2.8 in the final microcrystalline aqueous suspension. Thus, the optimal molar ratio in the fluid, milky microcrystalline aqueous suspension is preferably between 1:2.2 (or 1:2.4) and 1:2.8.

In a simple and preferred embodiment according to the invention, the reconstitutable teverelix-TFA composition is provided as a unit dosage, e.g. in the form of a powder, and has a predefined molar ratio of teverelix to the counter-ion TFA which is below the molar ratio required for microcrystal formation, preferably between 1:1 and 1:1.85 and even more preferred above 1:1.3 and below 1:1.6, and wherein said unit dosage is reconstituted just prior to use by adding a fixed amount of aqueous reconstitution solution containing a sufficient amount of trifluoroacetate so that a predetermined molar ratio of teverelix to trifluoroacetate is achieved in the provided pharmaceutical formulation. Said predetermined molar ratio is preferably at least 1:2.1, preferably at least 1:2.2 and even more preferred about 1:2.4, thereby ensuring that the provided reconstituted suspension contains substantially no gel, or at least so small concentrations of gel that the reconstituted suspension can be used for injections.

Accordingly, another aspect of the invention features a package e.g. a syringe or vial, filled with a unit dosage of the reconstitutable teverelix-TFA composition. Within the context of the present invention the term "unit dosage" is the amount of an active ingredient (teverelix) administered to a patient in a single dosage. Said unit dosages is e.g. placed in a suitable syringe in order to provide an easy administration.

BRIEF DESCRIPTION OF DRAWINGS

Preferred features of the invention are now described in connection with the appended drawing figures, wherein:

FIG. 1 shows the microcrystalline content of the aqueous teverelix-TFA compositions observed under a polarized microscope.

DETAILED DESCRIPTION OF THE INVENTION

Figure 1A:
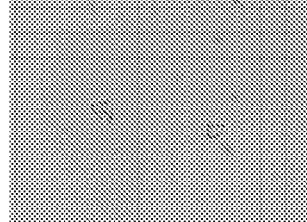
FIGS. 1a-1g are described in the Table 3.
Figure 1B:
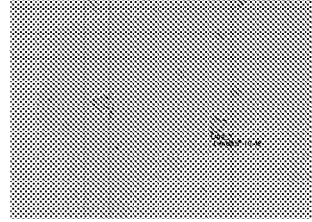
Figure 1C:
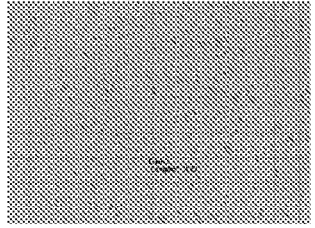
Figure 1D:
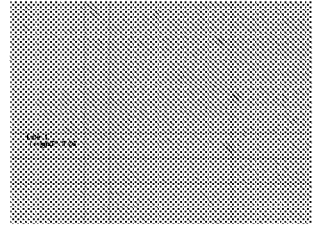
Figure 1E:
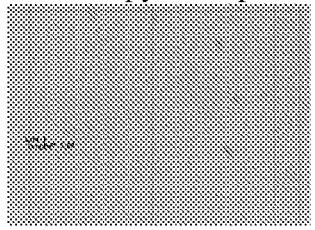
Figure 1F:
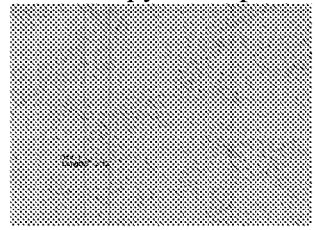
Figure 1G:
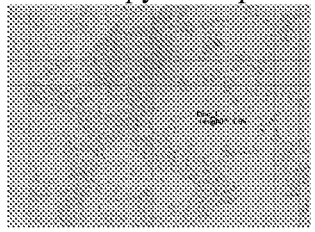

It has been found that the plasma concentration of teverelix in different patients is substantially independent of the patients weight, and it is accordingly believed that a unit dosage of teverelix is considered to be universal for all subjects (men/women). The dosage of teverelix in the suspension therefore depends on the condition to be treated.

Preferably the concentration of teverelix in said unit dosage is between 30 mg/ml and 100 mg/ml, and even more preferred between 45 mg/ml and 90 mg/ml, e.g. about 75 mg/ml. The concentration of teverelix may in some situations be higher than about 100 mg/ml. The volume of the unit dosage may be between 0.4 ml and 1.6 ml, e.g. about 1.2 ml. Injection given subcutaneous and/or intramuscularly at this concentration and volume, has proven to only provide a mild injection site reaction.

The final fluid, milky microcrystalline aqueous suspension according to the invention, e.g. when comprises in a pharmaceutical composition, is especially suitable for treating prostate cancer through a suppression of gonadotropins such as testosterone and dihydrotestosterone (DHT). The suspension may however equally well be used to at least partially ameliorating other diseases or condition related to the release of a gonadotropin hormone. Said disease or condition may be benign prostatic hyperplasia; acute urinary retention; endometriosis; breast, or cervical cancer; a hormone imbalance; an androgen-sensitive condition; an estrogen sensitive condition; or a combination thereof.

In a preferred embodiment the invention also relates to a kit, comprising a first package filled with a unit dosage of the teverelix-TFA composition, and a second package filled with a reconstitution solution comprising a sufficient amount of TFA for obtaining the desired molar ratio of at least 1:2.1, preferably at least 1:2.2 and even more preferred about or above 1:2.4. Preferably the molar ratio is not above 1:2.8, i.e. for each mol of teverelix the molar content of TFA is at or below 2.8. Said first package may e.g. be a syringe and the second package may be physically connected to said syringe in order to ensure that the correct molar ratio of teverelix to TFA is obtained. As one example of a first and second package which is physically connected to each other can be mentioned a conventional dual chamber syringe for lyophilised products. Such dual chamber syringe is well known in the art.

In one embodiment said kit is arranged for providing a final teverelix-TFA formulation having a molar ratio of teverelix to counter-ion of 1:2.4, having a teverelix concentration of about 75 mg/ml.

The compositions and formulations provided in the present invention is inexpensive to manufacture, and due to the ease of use it provides a very simple dosage regime.

Modifications and combinations of the above principles and combinations are foreseen within the scope of the present invention.

EXAMPLES

In order to establish the influence of the molar ratio of teverelix to the counter-ion trifluoroacetate a number of tests were performed.

Example 1: Preparation of Teverelix-TFA Compositions with Different Molar Ratio A custom-manufactured batch (Batch A) of teverelix with low TFA content was obtained. The characteristics of Batch A are shown in table 1.

TABLE 1

| Purity | 99.3% |
|---|---|
| Teverelix content | 85.56 weight-% |
| TFA content | 10.9 weight-% |
| Acetate content | 0.3 weight-% |
| Water content | 4.3 weight-% |

If a composition containing 75 mg teverelix is desired, composition A, then 88.28 mg of batch A has to be used, calculated as follows:

$$\frac{75 \text{ mg teverelix}}{99.3/100 \text{ (\% purity)} \times 85.56/100 \text{ (\% teverelix content)}} = 88.28 \text{ mg}$$

The molar ratio of teverelix to TFA in composition A can then be calculated.

The TFA content in 88.28 mg of batch A can be calculated to:

$$88.28 \text{ mg} \times 10.9/100 \text{ (TFA content in \%)} = 9.62 \text{ mg}$$

Since the molar mass of TFA, $M_{TFA}$, is 114 g/mol, and the molar mass of teverelix, $M_{TEV}$, is 1459 g/mol, the molar concentration of TFA in the 75 mg teverelix composition can be calculated to 0.084 mmol and the molar concentration of teverelix to 0.051 mmol. Thus, the molar ratio of teverelix to TFA in the reconstitutable composition A is 1:1.64, i.e. 1 mol teverelix to 1.64 mol TFA.

In order to prepare a number of different aqueous teverelix-TFA compositions with different molar ratios, twenty-one samples containing 44.14 mg+5% (41.93 to 46.35 mg) of composition A were accurately weighed in 2 ml glass tubes having a cap through which a reconstitution solution could be added by means of a micropipette.

Seven TFA reconstitution solutions containing TFA in 5% mannitol were prepared using a TFA composition obtained from Acros Organics, Geel, Belgium. Said TFA composition were 99% pure and had a density of 1.535 g/ml. The respective reconstitution solutions are shown in Table 2.

TABLE 2

| Solution | A | B | C | D | E | F | G |
|---|---|---|---|---|---|---|---|
| TFA mol/L | 0 | 0.01 | 0.023 | 0.036 | 0.049 | 0.062 | 0.075 |

The respective aqueous teverelix-TFA compositions were prepared by adding 0.5 ml of each of the above reconstitution solutions though the cap of the twenty-one glass tubes containing 44.14 mg+5% (41.93 to 46.35 mg) of composition A using a micropipette, i.e. three aqueous teverelix-TFA compositions having the same molar ratio were prepared. The mixtures were stirred using a vortex for 1 minute, and the solutions were observed visually for 10 minutes in order to establish if the desired fluid, milky microcrystalline homogeneous aqueous suspension of the teverelix-TFA, were obtained, or if a gel was formed instead. The results are summarised in Table 3:

TABLE 3

| Tubes | Molar ratio | Formation of gel | Microcrystalline formation | Formation of milky suspension | homogeneous suspension |
|---|---|---|---|---|---|
| A1, A2, A3 | 1:1.64 | yes | no | no | — |
| B1, B2, B3 | 1:1.85 | yes | no | no | — |
| C1, C2, C3 | 1:2.1 | no | yes | yes | no |
| D1, D2, D3 | 1:2.36 | no | yes | yes | yes |
| E1, E2, E3 | 1:2.61 | no | yes | yes | yes |
| F1, F2, F3 | 1:2.86 | no | yes | yes | yes |
| G1, G2, G3 | 1:3.12 | no | yes | yes | yes |

The microcrystalline content of the aqueous teverelix-TFA compositions in the No. 1 test tubes were further observed under a polarized light microscope supplied by Realux, France. The results for the respective molar ratio are shown in FIG. 1a-FIG. 1g. From these observation; it is clear that microcrystalline formation is not observed for the molar ratios of 1:1.85 and below, thus the molar ratio of teverelix to the counter-ion TFA has to be above at least 1:1.85 in order for the desired microcrystalline formation to be initiated.

It is accordingly preferred that the molar ratio of teverelix to trifluoroacetate (TFA) in the reconstitutable composition according to the invention is below 1:1.85 and preferable below 1:1.6.

Furthermore, as is evident from table 3, a homogeneous suspension of teverelix-TFA was not obtained until the molar ration was above 1:2.1, thus it is accordingly preferred that the molar ratio in the reconstituted aqueous teverelix-TFA suspension is above 1:2.1 and preferably even higher such as at least 1:2.2, and even more preferred at least 1:2.4.

Example 2: Content of Soluble Teverelix and Insoluble Teverelix in Relation to the Molar Ratio In order to determine the content of soluble teverelix in relation to insoluble teverelix in the respective test tubes, the No. 2 and No. 3 test tubes for each molar ratio were centrifuged at 10,000 rpm for 10 to 20 minutes, and the concentration of teverelix in the supernatant and pellet were measured using a HPLC analysis.

The chromatographic conditions for the HPLC analysis is shown in table 4.

| Column | Type (Aptys N°) | Lichrospher 100 RP18 (N°128) |
|---|---|---|
| | Particles size | 5 μm |
| | Diameter | 4 mm |
| | Length | 125 mm |
| Pre-Column | Type | Lichrocart 100 RP18 |
| | Particles size | 5 μm |
| | Diameter | 4 mm |
| | Length | 4 mm |
| Mobile Phase | | Acetonitrile/Water/TFA (35:65:0.1 V/V/V) |
| Injector cleaning | | Acetonitrile/Water (50:50 V/V) |
| Flow | | 1.0 mL/min |
| Pressure | | Approx. 65 bars |
| Oven Temperature | | 30° C. |
| Wavelength | | 210 nm |
| Injection volume | | 10 μL |
| Injector temperature | | 20° C. |
| Retention time of Teverelix | | Approx. 5.6 min |

Two 100% standards were prepared by weighing 59.9 mg teverelix acetate (batch 080113) in a volumetric flask and completing the volume to 100 ml with water:acetonitrile 65:35 v/v. 10 ml of this solution were completed to 50 ml with the same solvent, providing a concentration of 0.1 mg/ml teverelix peptide.

A 1% standard solution was prepared by diluting 2 ml of the 100% standard to 200 ml with the same solvent providing a concentration of 0.001 mg/ml teverelix peptide.

Internal standardization was carried out using the two 100% standards. The 1% standard was used to check the linearity of the response. Recovery with the 100% standard must be in the interval 95%-105%.

The pellet obtained after centrifugation was solubilised in water:acetonitrile 65:35 v/v, and the volume was completed to 100 mL with the same solvent. This solution was diluted by 5 (10 mL in 50 mL) and HPLC was performed.

The supernatant was transferred to a volumetric flask and the volume was completed to 100 mL with the same solvent, i.e. water:acetonitrile 65:35 v/v. This solution was diluted by 5 (10 mL in 50 mL) and HPLC was performed. The results of the HPLC analysis is shown in table 5.

TABLE 5

| Test tube | Molar ratio | Supernatant-Teverelix concentration (mg/ml) | Pellet-Teverelix concentration (mg/ml) |
|---|---|---|---|
| A2 | 1:1.64 | 52.0 | N/A |
| A3 | 1:1.64 | 58.5 | N/A |
| B2 | 1:1.85 | 57.2 | N/A |
| B3 | 1:1.85 | 60.3 | N/A |
| C2 | 1:2.1 | 25.9 | 26.9 |
| C3 | 1:2.1 | 26.1 | 25.5 |
| D2 | 1:2.36 | 9.4 | 39.3 |
| D3 | 1:2.36 | 8.3 | 44.9 |
| E2 | 1:2.61 | 5.4 | 50.8 |
| E3 | 1:2.61 | 7.2 | 51.6 |
| F2 | 1:2.86 | 3.7 | 56.2 |
| G3 | 1:2.86 | 3.6 | 58.4 |
| G2 | 1:3.12 | 1.5 | 53.6 |
| G3 | 1:3.12 | 1.2 | 58.4 |

Figure 2:
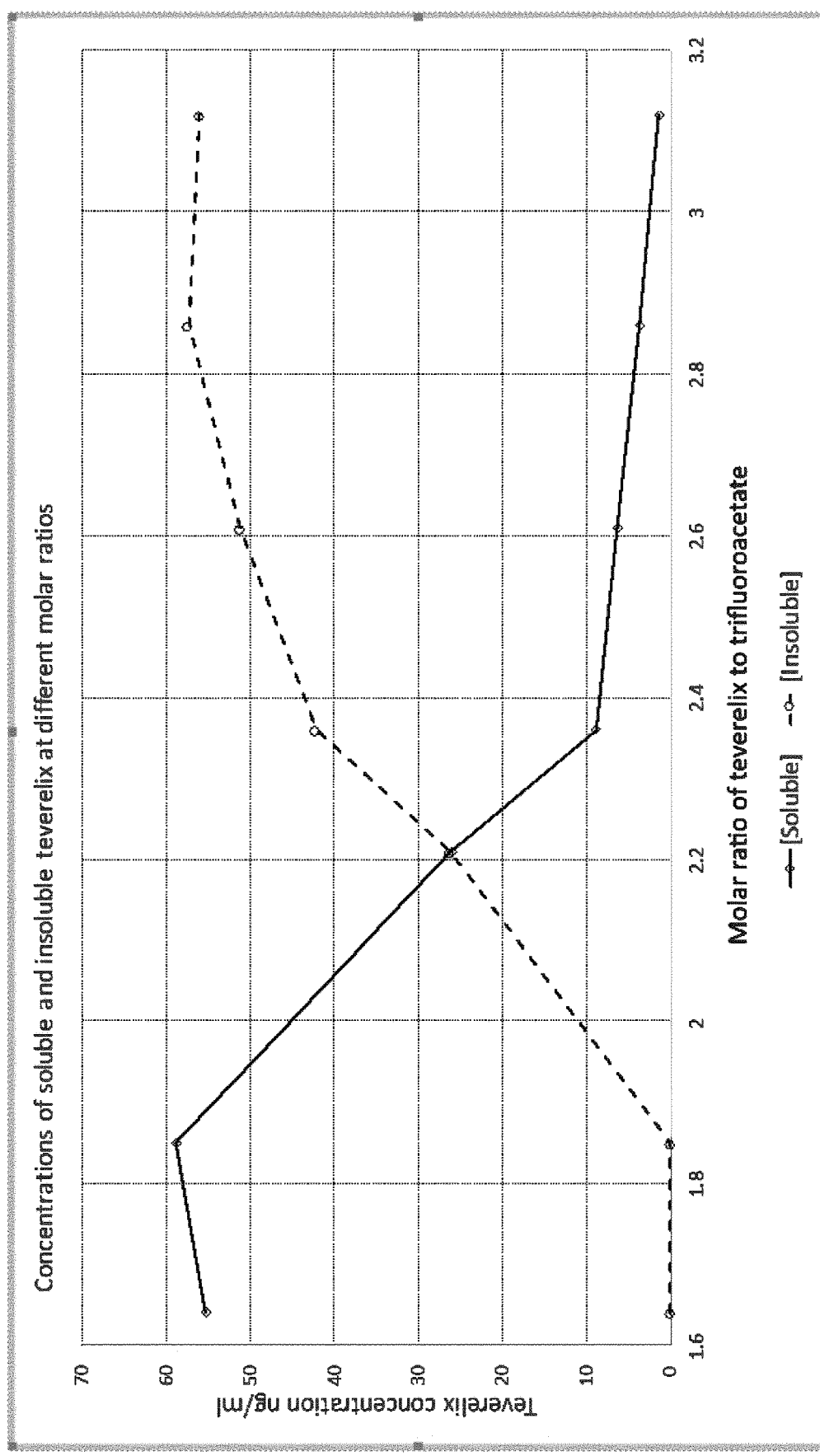
FIGS. 2 and 3 show Teverelix-TFA compositions with different molar ratios.
Figure 3:
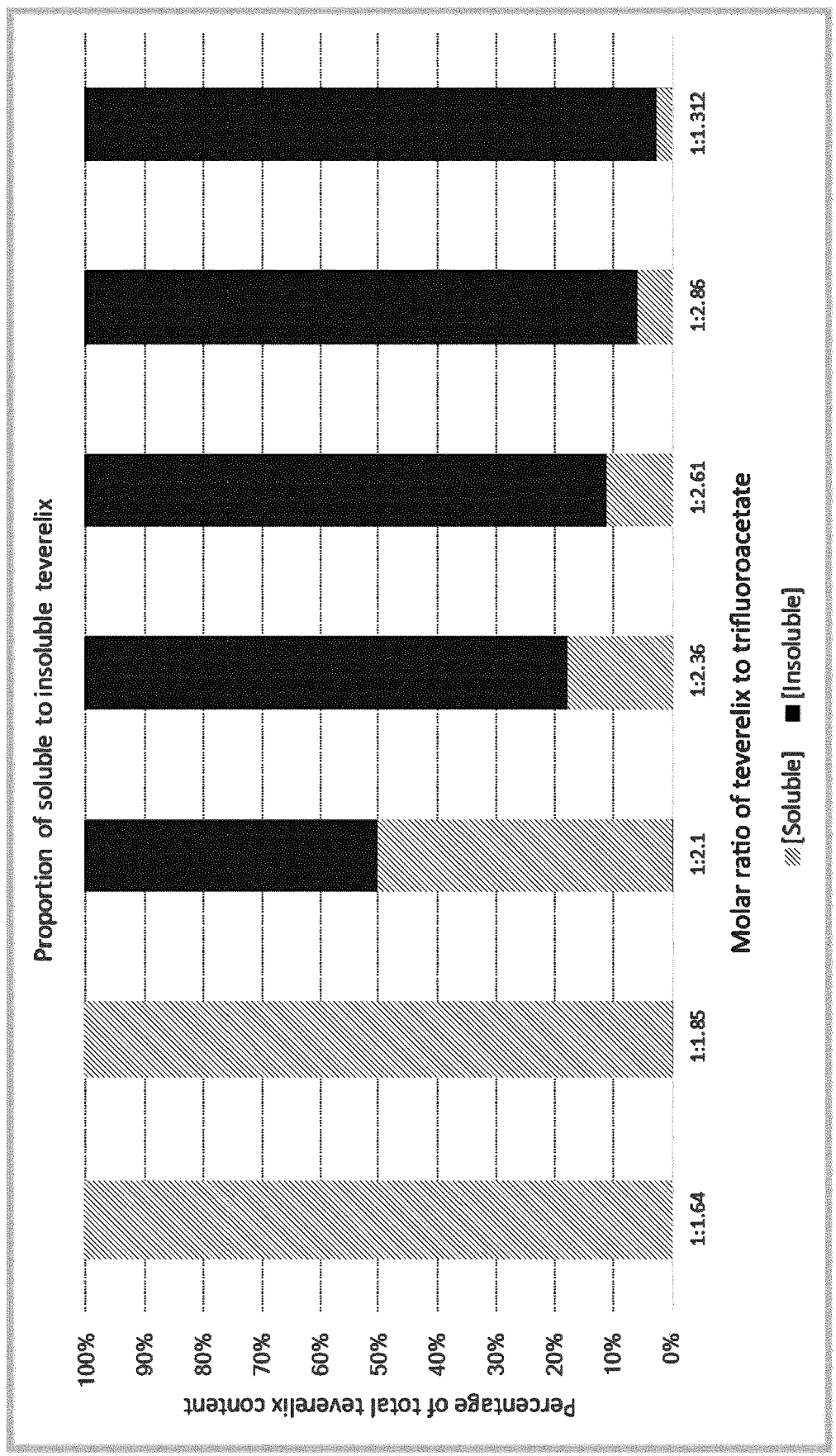

The average concentrations of each molar ratio were calculated, see table 6, and the results are depicted in FIGS. 2 and 3.

TABLE 6

| Test tube | Molar ratio | Supernatant-Average Teverelix concentration (mg/ml) | Pellet-Average Teverelix concentration (mg/ml) | Total (pellet + supernatant) Teverelix concentration (mg/ml) |
|---|---|---|---|---|
| A | 1:1.64 | 55.3 | N/A | 55.3 |
| B | 1:1.85 | 58.8 | N/A | 58.8 |
| C | 1:2.1 | 26.0 | 26.2 | 52.2 |
| D | 1:2.36 | 8.9 | 42.1 | 51.0 |
| E | 1:2.61 | 6.3 | 51.2 | 57.5 |
| F | 1:2.86 | 3.7 | 57.3 | 61.0 |
| G | 1:3.12 | 1.4 | 56.0 | 57.4 |

As is evident from table 5, and 6, and FIGS. 2 and 3, the degree of insoluble teverelix increases when the amount of trifluoroacetate increases in relation to teverelix, thus at a molar ratio of 1:2.1 (1 mol teverelix to 2.1 mol TFA), about 50% of the pharmaceutical formulation consist of insoluble teverelix, whereas the amount of insoluble teverelix is about 82% at a molar ratio of 1:2.36 (~1:2.4) in the pharmaceutical formulation.

Example 3: Plasma Concentration in Relation to the Molar Ratio

In order to evaluate the relevance of the molar ratio on the plasma concentration of teverelix, five glass vials containing different molar ratios were prepared as discussed in example 1, and the test tubes comprising the aqueous teverelix-TFA compositions shown in table 7 were provided:

TABLE 7

| Tube | I | II | III | IV | V |
|---|---|---|---|---|---|
| Molar ratio | 1:1.64 | 1:2.1 | 1:2.36 | 1:2.61 | 1:2.86 |

Five rats were tested with each molar ratio. Each rat was injected with 60 μl of the respective solutions using a 25 mm 21G luer 6% regular bevel needle (obtainable from Terumo, Leuven, Belgium) and 100 μl luer slip syringe (obtainable from Hamilton Company, Reno, USA). Plasma concentrations were measured prior to administration, then at 1 h, 6 h, 24 h, 48 h, 7 days, 10 days, 14 days, 21 days and 28 days following administration.

Figure 4:
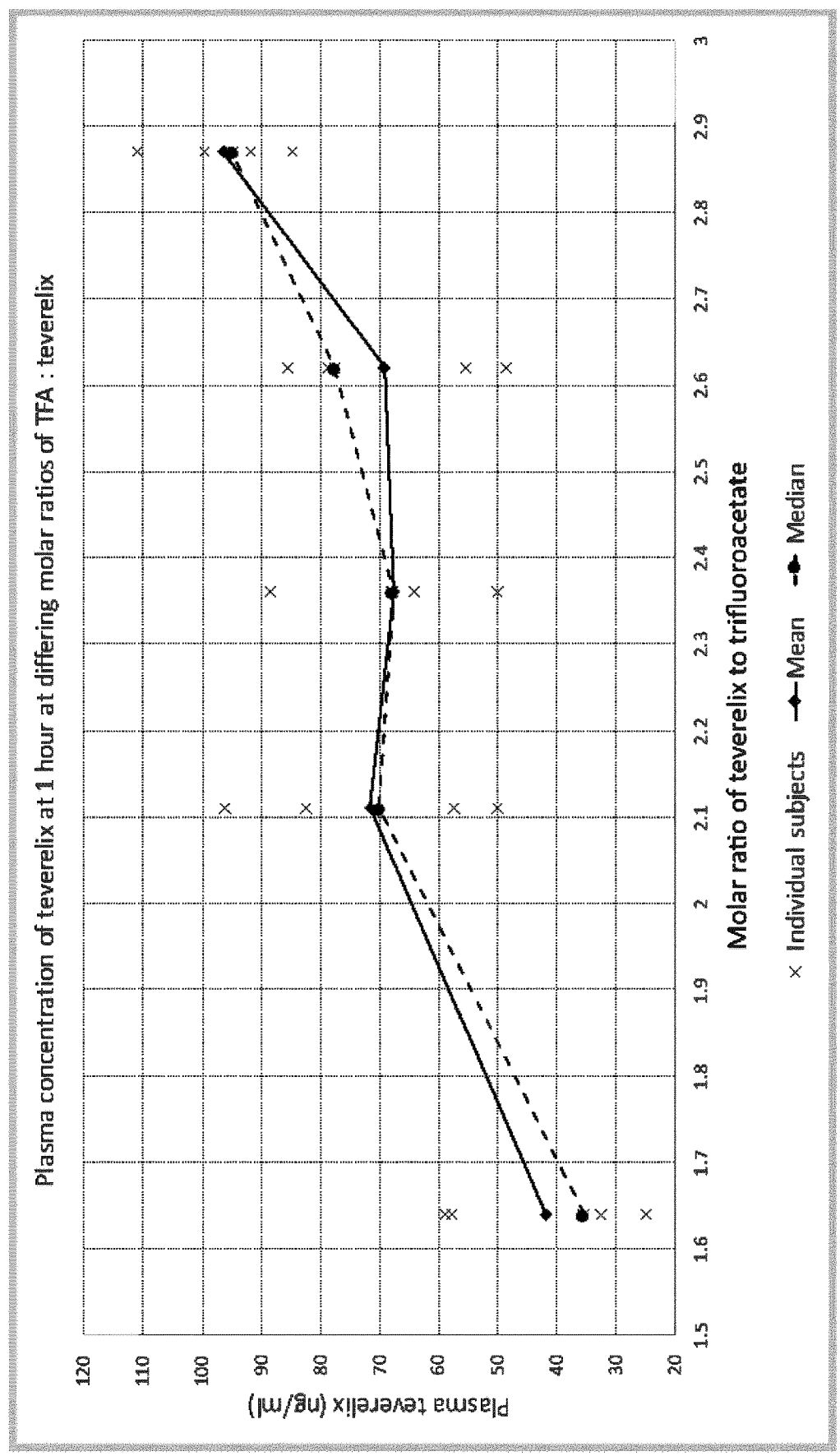
FIG. 4 show plasma concentration of teverelix at 1 hour at differing molar ratios of TFA:teverelix.

The peak plasma concentrations, Cmax, of teverelix after injection to each individual rat are shown in table 8, and depicted in FIG. 4.

TABLE 8

| Test tube | Molar ratio | Cmax | Cmax | Cmax | Cmax | Cmax | Cmax mean | Cmax median |
|---|---|---|---|---|---|---|---|---|
| I | 1:1.64 | 57.6 | 58.8 | 35.4 | 32.5 | 25 | 41.86 | 35.4 |
| II | 1:2.1 | 96 | 82.6 | 57.4 | 50.1 | n.a. | 76.525 | 70 |
| III | 1:2.36 | 67.6 | 50 | 67.9 | 64.2 | 38.6 | 67.66 | 67.6 |
| IV | 1:2.61 | 78.8 | 48.6 | 85.5 | 77.5 | 55.3 | 69.14 | 77.5 |
| V | 1:2.86 | 111 | 99.7 | 94.9 | 91.9 | 34.8 | 96.46 | 94.9 |

As is clear from these results the Teverelix Cmax increases until a molar ratio of 1:2.1 after which the plasma concentration is substantially stable.

The plasma concentration over a four week period, was also measured by taking blood samples at regular intervals.

Figure 5:
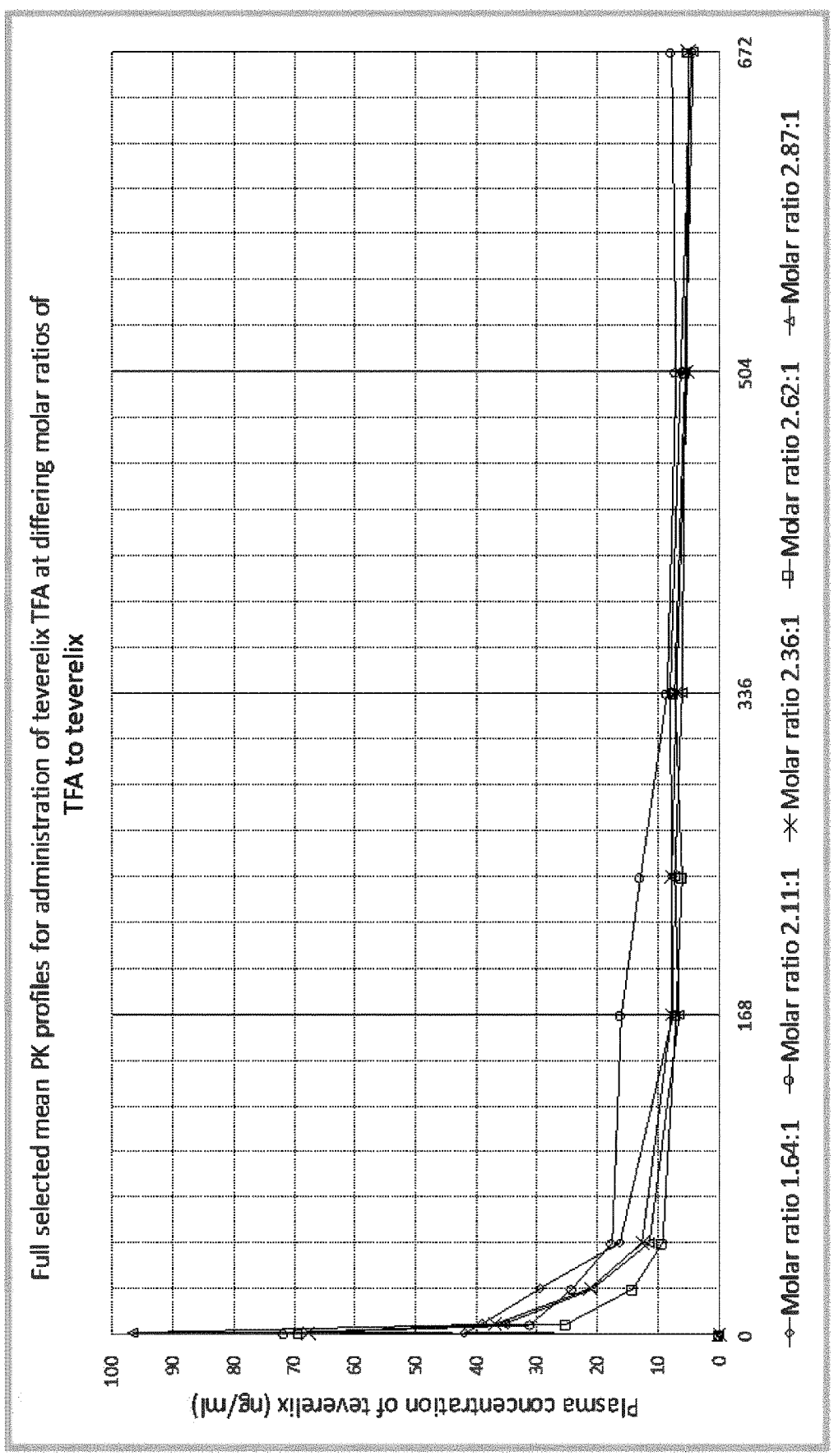
FIG. 5 shows full selected mean PK profiles for administration of teverelix TFA at differing molar ratios of TFA to teverelix.

The mean plasma levels in a four weeks period is shown in FIG. 5, and it is clear that the release profile of teverelix is dependent on the molar ratio. For instance, a higher plasma concentration of teverelix is shown with the suspension having a molar ratio of 1:2.1. Thus, it is possible to adjust the release profile of teverelix simply by adjusting the amount of trifluoroacetate added to the reconstitutable composition according to the invention, thereby changing the molar ratio of teverelix to trifluoroacetate in the pharmaceutical formulation.

Clinically this offers the potential of optimising the therapy to the requirements of individual groups of patients e.g. relating to different indications, age and/or gender. One patient group may need an immediate onset of action, requiring a high concentration of soluble teverelix, whereas another group may require a sustained release of teverelix, requiring a low concentration of soluble teverelix. In a similar manner, different pharmaceutical formulations having different molar ratios may be administered at different stages of a patients treatment. Furthermore, the possibility of adjusting the molar ratio to specific needs of different patient groups, will increase patient acceptance and compliance of therapy.

Example 4: Stability of Teverelix in Relation to the Molar Ratio

In order to establish the influence of the molar ratio of teverelix to the counter-ion trifluoroacetate on the stability of teverelix, the following test was performed.

Four batches of teverelix TFA solutions were prepared with differing molar ratios of teverelix to TFA (low: 1:1.7; mid-range: 1:2.16; high 1:2.8; and extreme: 1:4.0) at two concentrations: 10 mg/mL (expressed as base teverelix) and 1 mg/mL (expressed as base teverelix).

A reconstitutable Teverelix TFA composition, supplied as a dried powder, was obtained. The characteristics of the batch are shown in table 9:

TABLE 9

| Teverelix content | 79.8% |
|---|---|
| TFA content | 13.5% |
| Water content | 3.1% |

The molar ratio of the starting material was determined using the following calculation:

$$\frac{\text{Teverelix content/molecular weight of teverelix}}{\text{TFA content/molecular weight of TFA}} \Rightarrow \frac{79.8/1459}{13.1/114} = \frac{1}{2.16} = 1:2.16$$

The eight batches, one for each of the four molar ratios of 10 mg/ml, and one for each of the four molar ratios of 1 mg/ml, were prepared as follows.

Low Molar Ratio (1:1.7) at 10 mg/mL 1. 0.312 g of teverelix TFA (net weight teverelix) was reconstituted with water for injection, making the suspension up to 3.0 mL to form an 0.104 mg/mL homogenous milk suspension. Previous investigations demonstrate that at this concentration 96% of the teverelix will form solid teverelix, therefore approximately 300 mg of teverelix will be recovered as solid teverelix following centrifugation.

2. The preparation was immediately centrifuged for 10 minutes at 10,000 rpm (8,500 g) at 4° C.

3. The supernatant from the centrifuged material was discarded. Previous investigations have demonstrated that the solid teverelix has a molar ratio of approximately 1:1.7 teverelix to TFA.

4. The centrifugation pellet was resuspended with water for injection and made up to 30 mL to form a solution of approximately 10 mc/mL and a molar ratio of approximately 1:1.7.

Mid-Molar Range Ratio (1:2.16) at 10 mg/mL 1. 0.1 g of teverelix TFA (net weight teverelix) was reconstituted with water for injection in a 10 mL conical flask to make a solution of 10.0 mL volume to form a solution of teverelix at 10 mg/mL and a molar ratio of 1:2.16 teverelix to TFA.

High Molar Ratio (1:2.8) at 10 mg/mL 1. 0.1 g teverelix TFA (net weight teverelix) was reconstituted with 5 mL of 0.0097 M trifluoroacetic acid in water for injection in a 10 mL conical flask 2. The solution was made up to 10.0 mL with water for injection to form a solution of teverelix at 10 mg/mL and a molar ratio of 1:2.8 teverelix to TFA.

Extreme Molar Ratio (1:4.0) at 10 mg/mL 1. 0.1 g teverelix TFA (net weight teverelix) was reconstituted with 5 mL of 0.0252 M trifluoroacetic acid in water for injection in a 10 mL conical flask 2. The solution was made up to 10.0 mL with water for injection to form a solution of teverelix at 10 mg/mL and a molar ratio of 1:4.0 teverelix to TFA.

Low Molar Ratio (1:1.7) at 1 mg/mL 1. 0.312 g of teverelix TFA (net teverelix) was reconstituted with water for injection, making the suspension up to 3.0 mL to form an 104 mg/mL homogenous milk suspension.

2. The preparation was immediately centrifuged for 10 minutes at 10,000 rpm (8,500 g) at 4° C.

3. The supernatant from the centrifuged material was discarded

3. The centrifugation pellet was resuspended in water for injection (final volume 300 mL) to make up a solution of approximately 1 mg/mL and a molar ratio approximately 1:1.7 teverelix to TFA.

4. 10.0 mL was transferred to a 10 mL cenical flask.

Mid-Molar Range Ratio (1:2.16) at 1 mg/mL
1. A 1 mg/mL solution of teverelix TFA in water for injection was prepared High Molar Ratio (1:2.8) at 1 mg/mL
1. 0.010 g teverelix TFA (net weight teverelix) was reconstituted with 5 mL of a 0.001 M trifluoroacetic acid in water for injection in a 10 mL conical flask
2. The volume was completed to 10 mL with WFI Extreme Molar Ratio (1:4.0) at 1 mg/mL
1. 0.010 g teverelix TFA (net weight teverelix) was reconstituted with 5 mL of a 0.0205 M trifluoroacetic acid in water for injection in a 10 mL conical flask
2. The volume was completed to 10 mL with WFI All of the solutions were kept at lab temperature (20° C.) before analyses for teverelix purity.

Samples was taken from each solution in duplicate and analysed for teverelix purity using a conventional RP-HPLC method. The chromatic conditions were as shown in table 10:

TABLE 10

| Column | Phenomenex Aqua C18 150 2.0 mm, 3 μm, 125Å, LCC-012 |
| --- | --- |
| Column temperature | 65° C. |
| Autosampler temperature | 4° C. |
| Flow rate | 0.3 ml/min |
| Injection volume | 3 μl |
| Run time | 60 minutes |
| Detection | UV detection, 226 nm |

The purity of teverelix in the solutions after preparation, i.e. at time zero, is shown in table 11:

TABLE 11

| Molar ratio | 10 mg/mL Time 0 | 1 mg/mL Time: 0 |
| --- | --- | --- |
| 1:1.7 | 99.47% | 99.58% |
| 1:2.16 | 99.45% | 99.49% |
| 1:2.8 | 99.48% | 99.48% |
| 1:4.0 | 99.47% | 99.48% |

In order to evaluate the stability over time, the respective solutions were then stored in stoppered glass conical flasks in a chamber at +40° C. and a relative humidity of 75%.

After one month for the 10 mg/mL solutions, and two weeks for the 1 mg/mL solutions, teverelix purity analysis was repeated using the method already described. The purity of the solutions after the relevant period, is presented in table 12 below.

TABLE 12

| Molar ratio | 10 mg/mL Time: 1 month | 1 mg/mL Time: 15 days |
| --- | --- | --- |
| 1:1.7 | 97.49% | 98.92% |
| 1:2.16 | 95.99% | 98.68% |
| 1:2.8 | 93.49% | 98.37% |
| 1:4.0 | 86.16% | 97.97% |

Figure 6:
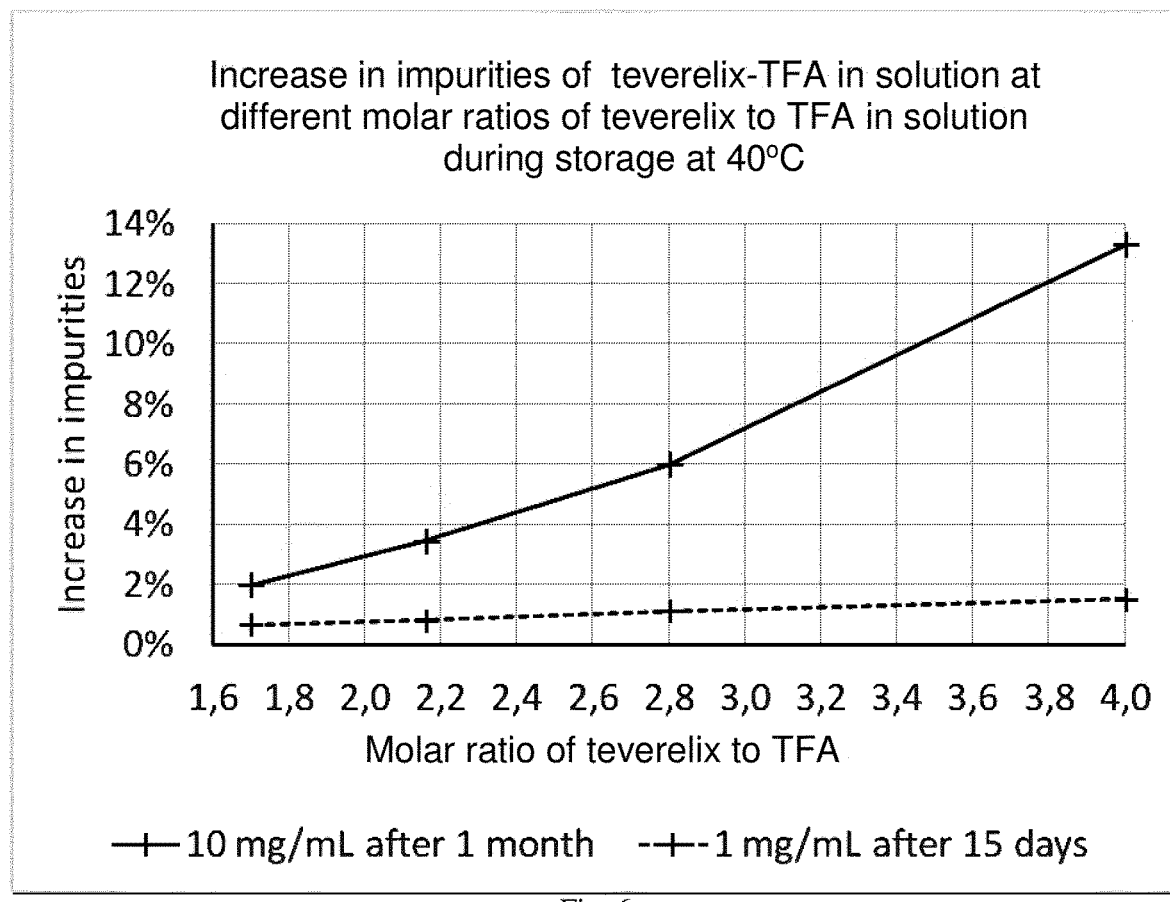
FIG. 6 shows increase in impurities of teverelix-TFA in solution at different molar ratios of teverelix to TFA in solution during storage at 40° C.
Figure 7:
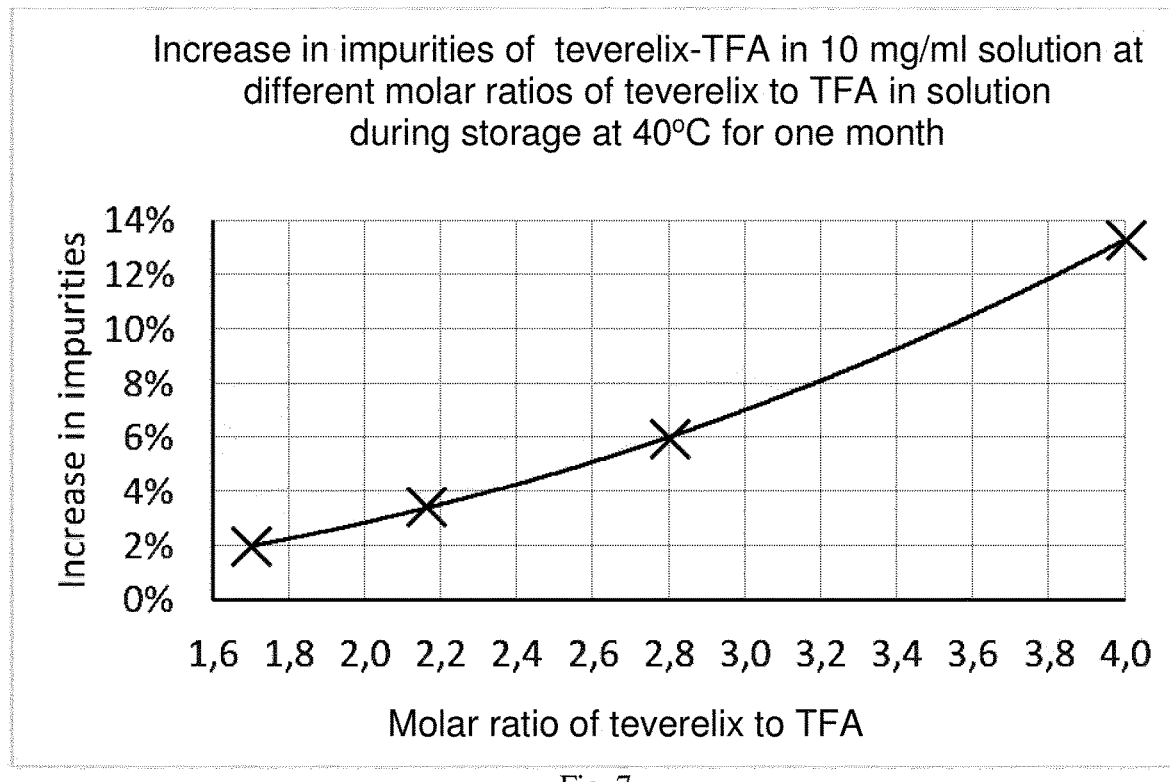
FIG. 7 shows increase in impurities of teverelix-TFA in 10 mg/ml solution at different molar ratios of teverelix to TFA in solution during storage at 40° C. for one month.

The stability results are shown in FIGS. 6 and 7, and depicts the increase in percentage of impurities during storage according to the molar ratio of the suspension.

From said figures it is clear that higher concentrations of trifluoroacetate in the suspensions provides significantly higher concentrations of impurities, thus the results verify that when teverelix is placed in contact with high concentrations of acid (trifluoroacetate), undesirable degradation products (impurities) will appear in small amounts and may potentially influence quality, safety and efficacy of the formulation, thereby potentially causing serious health hazards. Thus, in order to obtain a stable teverelix-TFA composition, both as dry powder and as a suspension/solution, it is important to provide a composition with a low concentration/content of trifluoroacetate, i.e. for each mol of teverelix the molar content of trifluoroacetate should be kept as low as possible.

From FIGS. 6 and 7, it can be seen that when the molar ratio of teverelix to trifluoroacetate is below 1:2.8, (i.e. 1 mol teverelix to less than or equal to 2.8 mol TFA) in the suspension, the level of impurities, i.e. undesirable degradation products e.g. caused by deamidation are kept at an acceptable level.

It is also clear from said figures, that the concentration of teverelix is also relevant for the level of impurities. However, in order to reduce the injections volumes, it is relevant to have suspensions comprising concentrations of teverelix of at least 10 mg/ml preferably at least 30 mg/ml, thus it is not practically possible simply to reduce the concentration of teverelix in the final fluid, milky aqueous suspension. However, this factor only makes the concentration of acid (trifluoroacetate) in the composition even more important during storage, in both the dry and liquid state, in order to provide a stable product.

The invention claimed is:

1. A stable reconstitutable teverelix-TFA composition having a molar ratio of teverelix (Ac-D-Nal-D-pClPhe-D-Pal-Ser-Tyr-D-Hci-Leu-Lys(iPr)-Pro-D-Ala-NH2) to trifluoroacetate below the molar ratio required for microcrystal formation,
wherein the composition comprises between 1.3 mol trifluoroacetate and 1.6 mol trifluoroacetate per mol teverelix,
wherein the reconstitutable composition is a powder,
wherein water is present in the reconstitutable teverelix-TFA composition in an amount between 0.3% and 5% by weight based on the total weight of the reconstitutable teverelix-TFA composition, and
wherein the composition forms a gel without any insoluble teverelix in the form of microcrystals.

2. The reconstitutable composition according to claim 1, wherein water is present in the reconstitutable teverelix-TFA composition in an amount between 1% by weight and 2% by weight.

3. The reconstitutable composition according to claim 1, wherein the powder of the reconstitutable composition is obtained by lyophilization or spray-drying and/or a cake obtained by lyophilization.

4. A method of preparing the reconstitutable teverelix-TFA composition according to claim 1, wherein said method comprises
mixing teverelix and trifluoroacetate at a molar ratio below the molar ratio required for microcrystal formation thereby providing an aqueous teverelix-TFA solution, wherein the composition comprises between 1.3 mol trifluoroacetate and 1.6 mol trifluoroacetate per mol teverelix,
drying the aqueous teverelix-TFA solution, and
wherein the aqueous teverelix-TFA solution is dried to an extent such that the provided reconstitutable teverelix-TFA composition comprises water in an amount between 0.3% and 5% by weight based on the total weight of the reconstitutable teverelix-TFA composition.

5. The method according to claim 4, wherein the molar ratio of teverelix to trifluoroacetate (TFA) is above 1:1.3 and below 1:1.6 in the aqueous teverelix-TFA solution such that for each mole teverelix in the composition the composition comprises above 1.3 mol trifluoroacetate and below 1.6 mol trifluoroacetate.

6. The method according to claim 4, wherein said method comprises the step of analysing the molar ratio in the aqueous teverelix-TFA solution prior to drying, and optionally adjusting the molar ratio of teverelix to trifluoroacetate (TFA) to a specific predefined molar ratio such that the composition comprises between 1.3 mol TFA and 1.6 mol TFA per mol teverelix, before said solution is dried.

7. A method of reconstituting the reconstitutable teverelix-TFA composition according to claim 4, wherein said method comprises adding an aqueous reconstitution solution to the reconstitutable teverelix-TFA composition and adjusting the molar ratio of teverelix to trifluoroacetate by adding trifluoroacetate for each teverelix in the composition, wherein the composition comprises at least 1.6 mol TFA.

8. The method according to claim 7, wherein the aqueous reconstitution solution comprises trifluoroacetate in an amount sufficient to provide a molar ratio of teverelix to trifluoroacetate of at least 1:1.6.

9. A package filled with the reconstitutable teverelix-TFA composition according to claim 1.

10. The package according to claim 9, wherein the package is a syringe suitable for providing a subcutaneous and/or intramuscularly injection.

11. A kit comprising a first package as defined in claim 9, and a second package filled with a aqueous reconstitution solution comprises trifluoroacetate in an amount sufficient to provide a molar ratio of teverelix to trifluoroacetate after reconstitution such that for each mole teverelix in the composition the composition comprises at least 1.6 trifluoroacetate.

12. The package according to claim 9, comprising a unit dosage of the reconstitutable teverelix-TFA composition according to claim 1.

* * * * *